United States Patent [19]

Pospisil et al.

[11] Patent Number: 5,395,237
[45] Date of Patent: Mar. 7, 1995

[54] ORTHODONTIC BRACKET WITH INTEGRAL BALL HOOK AND METHOD OF MAKING

[75] Inventors: Jirina V. Pospisil, Covina; Randy D. Collins, Claremont, both of Calif.

[73] Assignee: Minnesota Mining and Manufacturing Company, St. Paul, Minn.

[21] Appl. No.: 178,086

[22] Filed: Jan. 6, 1994

[51] Int. Cl.6 ............................................. A61C 3/00
[52] U.S. Cl. ................................... 433/8; 29/160.6
[58] Field of Search ................. 433/8, 9, 10, 11, 12, 433/13, 14; 29/160.6

[56] References Cited

U.S. PATENT DOCUMENTS

| | | |
|---|---|---|
| 2,713,720 | 7/1955 | Johnson. |
| 4,669,981 | 6/1987 | Kurz ............................. 433/9 |
| 5,095,602 | 3/1992 | Reher et al. ..................... 433/8 |
| 5,125,831 | 6/1992 | Pospisil .......................... 433/8 |
| 5,125,831 | 6/1992 | Pospisil .......................... 433/8 |
| 5,129,821 | 7/1992 | Schuetz .......................... 433/8 |
| 5,226,814 | 7/1993 | Allen ............................. 433/8 |
| 5,292,248 | 3/1994 | Schultz .......................... 433/8 |

OTHER PUBLICATIONS

Ormco Orthodontic Products catalog pages, Ormco Corporation, 1992.
Rocky Mountain Orthodontics Catalog No. 4, pp. E1-5–E17, E24–E25, E28–E29, E32–E33, RMO, Inc., 1992.
3M Unitek Catalog pp. 2-1, 2-4 and 3-7, 3M Unitek Corporation, 1990.

*Primary Examiner*—Cary E. O'Connor
*Attorney, Agent, or Firm*—Gary L. Griswold; Walter N. Kirn; James D. Christoff

[57] ABSTRACT

A machined orthodontic bracket has a hook integrally formed with a gingival tiewing of the bracket. The hook includes a square shank, and a head with a cylindrical surface. The hook is machined by an end mill or formed cutter, and is achieved in part by changing the orientation of the bracket midway through the machining operation.

9 Claims, 1 Drawing Sheet

U.S. Patent  Mar. 7, 1995  5,395,237
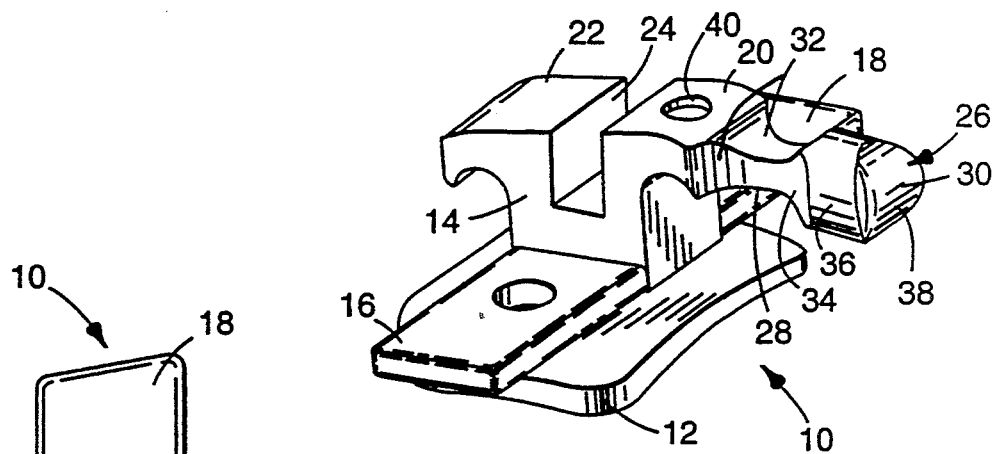
FIG.1
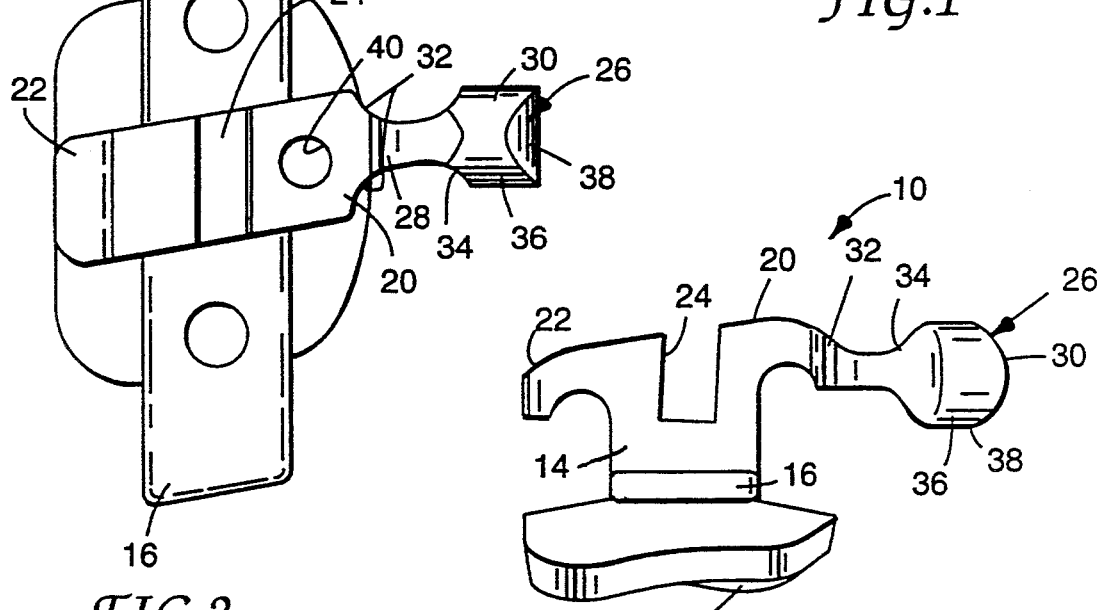
FIG.2
FIG.3
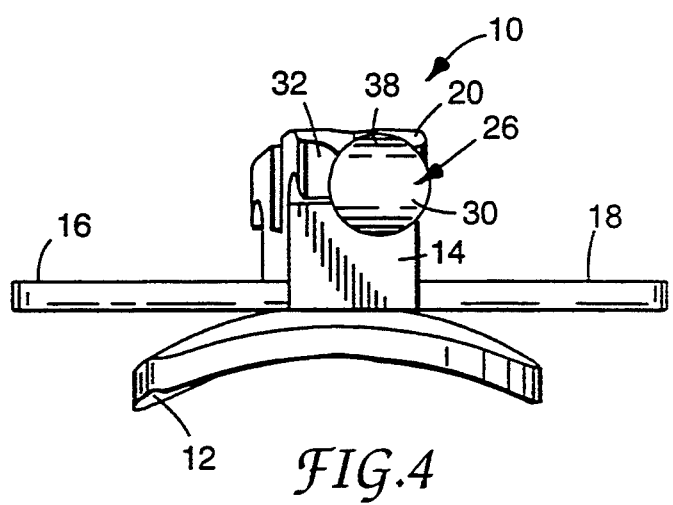
FIG.4

ORTHODONTIC BRACKET WITH INTEGRAL BALL HOOK AND METHOD OF MAKING

BACKGROUND OF THE INVENTION

1. Field of the Invention

This invention relates to a bracket that is attached to a tooth for orthodontic treatment, and particularly concerns a bracket having a ball hook that is integrally formed with a tiewing of the bracket.

2. Description of the Related Art

Orthodontic treatment involves movement of malpositioned teeth to desired positions for correct occlusion and improved aesthetics. During treatment, small slotted bodies known as brackets are affixed to the teeth and an archwire is secured in the slot of each bracket. The archwire serves as a track to guide movement of the teeth toward desired positions.

In some instances, a small hook is affixed to certain brackets for movement of the teeth in particular directions. One end of an elongated elastic member is connected to the hook, and the other end is connected to a hook mounted elsewhere such as on another bracket, on an archwire, or on another orthodontic appliance in the oral cavity. The elastic member is under sufficient tension when in place to provide a resilient force that urges the teeth in desired directions.

U.S. Pat. No. 5,125,831, assigned to the assignee of the present invention, describes an orthodontic bracket having four tiewings and a hook that is integrally connected to one of the tiewings. (Tiewings are tiny wings on the bracket that function to grasp an O-ring or a ligature wire that connects the archwire to the bracket.) The hook has opposed notches to provide connection to an elastic member extending in a direction away from either notch. The bracket described in U.S. Pat. No. 5,125,831 is similar to a bracket presently manufactured in a machining operation and sold by the assignee of the present invention under the trademark "UNI-TWIN".

The hook of the bracket shown in U.S. Pat. No. 5,125,831 has a generally flat configuration when viewed toward the mesial side of the bracket (i.e., toward the side of the bracket facing midline of the arch) or the distal side of the bracket (i.e., toward the side of the bracket facing away from the midline of the arch). However, other brackets having hooks termed ball hooks are also known; such hooks include a shank with an enlarged, somewhat spherical head, and the shank is elongated and has a generally circular configuration in transverse cross section. Optionally, the shank of such ball hooks can be bent by the orthodontist in a desired direction to decrease the likelihood that the elastic member does not unintentionally detach from the hook during treatment. Ball hooks are preferred by some orthodontists over flat hooks because the enlarged ball head provides better retention of the elastic member in some instances.

As can be appreciated, the strength of the ball hook, and especially of the shank, is a matter of significant importance. For example, if the shank breaks from the tiewing as the shank is bent to shift the hook to a certain orientation, the entire bracket must be detached from the tooth and replaced with a new assembly. Such a procedure is time consuming and a nuisance to both the orthodontist and the patient.

In some instances, the shanks of ball hooks are connected to a tiewing of the bracket by a brazing operation. However, brackets having a hook brazed to a tiewing are not entirely satisfactory, since the brazing is relatively expensive, and careful alignment of the small parts during brazing is needed. Also, errors during brazing operation may not be readily apparent, but may result in a weak joint between the shank of the hook and the tiewing such that the shank detaches from the bracket when bent.

In other instances, ball hooks are made integrally with the brackets when the brackets (including the hooks) are manufactured in a casting process or in a sintering operation. Cast and sintered brackets having integral ball hooks are generally less expensive to manufacture than brackets having brazed hooks, but there is a possibility that the shank of the hook may have insufficient strength as a result of the casting or sintering operation, due in part to the relatively small transverse cross-sectional areas of the shank. For example, when brackets are made by a metal injection molding operation, the metal powder may not flow and/or pack in a satisfactory manner in tiny cavities of the die that correspond to the shank of the resultant bracket hook, with the result that the strength of the shank is diminished.

SUMMARY OF THE INVENTION

The present invention concerns an orthodontic bracket that comprises a base, a body extending from the base and a tiewing extending from the body. The bracket includes a hook connected to the tiewing. The hook includes an elongated shank and a head. The head has a mesiodistal width that is greater than the mesiodistal width of the shank, and a labiolingual depth that is greater than the labiolingual depth of the shank. The hook and the tiewing are integrally formed during a machining operation.

The present invention also concerns a method for making an orthodontic bracket having a hook, and comprises the step of shaping round stock in a lathe to form surfaces generally corresponding to labial sides of an occlusal and a gingival tiewing of the bracket as well as to form surfaces generally corresponding to labial and lingual sides of a hook of the bracket. The method also includes the step of cutting the stock along spaced apart reference lines to form surfaces generally corresponding to mesial and distal sides of the occlusal and gingival tiewings of the bracket and also to remove portions of the stock located on mesial and distal sides of the hook. The method further includes the step of moving a cutting tool along a path generally parallel to the labial surface of the bracket to form surfaces generally corresponding to an occlusal edge of the occlusal tiewing, a gingival edge of the hook and a pair of notches of the hook. The method also includes the step of moving a cutting tool along a path about an axis generally perpendicular to the occlusal plane of the bracket to form surfaces generally corresponding to labial and lingual surfaces of a head of the hook.

The present invention is particularly advantageous in that the bracket is relatively inexpensive to manufacture, and can be made in automated fashion with little human attention. Yet, the hook of the bracket exhibits satisfactory strength in use. The integral, machined nature of the hook of the present invention avoids problems such as porosity or joint dysfunction as may be observed in connection with cast or sintered brackets, or in connection with brackets wherein a hook is brazed to a tiewing of the bracket. Moreover, machining of the bracket avoids the costs associated with making molds or dies such as are used to make brackets by a casting or sintering operation.

BRIEF DESCRIPTION OF THE DRAWINGS

FIG. 1 is a perspective view of a bracket made in accordance with the invention, showing labial, mesial and gingival sides of the bracket;

FIG. 2 is an elevational view of the bracket shown in FIG. 1, looking toward a labial side of the bracket;

FIG. 3 is an elevational view of the bracket shown in FIG. 1, looking toward a mesial side of the bracket; and FIG. 4 is a plan view of the bracket shown in FIG. 1, looking toward a gingival side of the bracket.

DETAILED DESCRIPTION OF THE PREFERRED EMBODIMENT

An orthodontic bracket constructed in accordance with the present invention is broadly designated by the numeral 10 in FIGS. 1-4. The bracket 10 includes a base 12 having a foil mesh bonding surface for directly bonding the bracket 10 to the surface of a tooth. The base 12 has a concave, compound contour that matches the convex shape of the tooth surface, and is somewhat similar to bonding bases sold under the trademark "DYNA-BOND II" (3M Unitek Corporation), except that the bonding base is smaller.

The bracket 10 includes a body 14 that extends from the base 12 in a buccolabial direction (i.e., in a direction toward the patient's cheeks or lips). A mesial (i.e., toward the middle of the dental arch) rotation arm 16 and a distal (i.e., in a direction away from the middle of the dental arch) rotation arm 18 are integrally connected to the body 14 directly adjacent the base 12.

A gingival tiewing 20 extends from the body 14 in a gingival direction (i.e., toward the gums). An occlusal tiewing 22 extends from the body 14 in a occlusal direction (i.e., toward the outermost end of the teeth). An archwire slot 24 is located between the tiewings 20, 22 and has a rectangular configuration in transverse cross-section in order to matingly receive an archwire having a similar rectangular cross-sectional configuration.

A hook 26 is integrally connected to the gingival edge of the gingival tiewing 20. The hook 26 includes a shank 28 having a longitudinal axis that extends in an occlusal-gingival direction parallel to the mesial and distal sides of the tiewings 22, 24. The outermost end of the hook 26 includes a head 30 that is connected to the gingival end of the shank 28.

The shank 28 has a generally rectangular cross-sectional configuration in views transverse to its longitudinal axis, and in the embodiment illustrated has a mesio-distal width of 0.016 inch (0.4 mm) and a labiolingual depth of 0,013 inch (0.3 mm), although other dimensions may also be used. The occlusal end of the shank 28 includes three fillets 32 (on mesial, distal and labial sides) that smoothly blend in curved fashion the transition between the gingival end of the gingival tiewing 20 and the reduced dimension of the central portion of the shank 28. The shank 28 also includes four fillets 34 (on mesial, distal, labial and lingual sides) that smoothly blend in curved fashion the transition between the central portion of the shank 28 and the occlusal side of the head 30.

The head 30 includes a cylindrical surface 36 that extends around mesial, labial, distal and lingual sides of the head 30 in smoothly curved fashion. An outermost end 38 of the head 30 has the shape of a partial cylinder that smoothly blends with edges of the cylindrical surface 36.

The rectangular cross-sectional shape of the shank 28 is an advantage when the hook 26 is adjusted in use, as the rectangular shape facilitates bending of the shank 28 in one of four particular directions, and hinders bending in other directions. More specifically, the shank 20 can be readily bent in a labial, lingual, mesial or distal direction so that the head 30 is moved labially, lingually, mesially, or distally respectively, as such directions correspond to the four flat sides of the shank 28. However, bending of the shank 28 in other directions is hindered due to the orientation of the rectangular cross-sectional shape of the shank 28. Such construction is an advantage over hooks having round shanks, since it is more likely that the head 30 of the present invention will be oriented in the desired direction after bending even in instances where the force exerted by the pliers or other bending tool is not exactly aligned in the proper direction.

Moreover, the fillets 32, 34 are an advantage when efforts are made to bend the hook 26, because the location of the bend is thus likely to occur in the central portion of the shank 28 between the fillets 32, 34 where the cross-sectional dimensions of the shank 28 are the smallest. As such, the resulting hook 26 when bent is more likely to have sufficient space in the "notches" of the hook 26 presented between the head 30 and the tiewing 20 to properly receive an elastic member and to thereafter retain the elastic member on the hook 26 during treatment.

The cylindrical outer surface 36 of the head 30 is an advantage from the standpoint of patient comfort. If, for example, the head 30 contacts the patient's cheeks, the cylindrical surface 36 is likely to touch the cheeks along a line corresponding to its outermost section. By way of comparison, a ball hook having a spherical head would be more likely to make point contact with the patient's cheeks, thereby increasing the chances that the patient will experience discomfort.

In making the bracket 10, a process somewhat like the machining process described in U.S. Pat. No. 2,713,720 (incorporated by reference herein) is employed during the initial stages, wherein a number of brackets are formed around the circumference of a ring that is cut from round bar stock. First, a length of solid round bar stock, made of 17.4 PH stainless steel, is mounted on a lathe. As the stock rotates, a boring cutter having a round nose is moved along a path to cut and shape the lingual side of the gingival tiewing 20, the lingual sides of the shank 28, and portions of the stock corresponding to areas lingually of the head 30 including the lingual half of the end 38. Next, a turning tool is moved along the outside to shape and cut portions of the stock corresponding to areas labially of the head 30 (including the labial half of the end 38), the labial side of the shank 28, and the labial sides of the tiewings 20, 22.

Next, a head spindle having a motor driven gripper is moved toward the stock to grip the labial side of the brackets 10 on the round stock in areas corresponding to gingival tiewings 20. A ring having a number of the partially formed brackets 10 is then cut from the bar stock. Subsequently, a cutter is used to shape areas corresponding to the lingual sides of the occlusal tiewing 22 as the ring is rotated by the spindle.

Next, the ring is mounted in a CNC (Computer Numerical Control) milling machine by grasping inside walls of the ring (corresponding to occlusal and gingival sides of the bracket bodies 14) by a collet. In the steps that follow, the ring is indexed in rotary fashion after each step (or group of steps, as appropriate) so that each step is repeated for each of the brackets 10 that is to be made along the various circumferential locations on the ring.

A rotary cutter, similar to a miniature circular saw, is used to cut the ring along pairs of spaced apart reference lines to form mesial and distal edges of the occlusal tiewing 22 and the gingival tiewing 20, as well as to remove portions of the ring located along mesial and distal sides of the hook 26. Optionally, a drill is used to drill holes in the rotation wings 16, 18. Next, a drill is deployed to form an identification dot 40 (FIGS. 1 and 2). If desired, a rotary cutting tool is activated to cut a scribe line if desired (not shown in the drawings). A rotary cutting tool is then activated to saw the archwire slot 24 at a particular orientation to provide proper torque and angulation for the bracket 10.

Next, the ring is turned about 90 degrees relative to the milling machine such that the shank 28 extends upwardly. Subsequently, a cutting tool is activated to rotate about a reference axis that is perpendicular to the occlusal plane (i.e., a reference plane located flatly between the patient's upper and lower dental arches when the bracket 10 is mounted on the patient's tooth). While rotating, the cutting tool also moves along a circular path about the aforementioned reference axis perpendicular to the occlusal plane and around the hook 26 such that the smooth cylindrical surface 36 on the head 30 is thereby formed. As illustrated in FIG. 2, the sides of the surface 36 are perpendicular to the occlusal plane and are oriented at an acute angle relative to the occlusogingivally extending sides of the tiewings 20, 22 in order to decrease the likelihood that an elastic member may slip off of the hook 26 during treatment.

Next, a cutting tool, rotating about an axis corresponding to a labiolingual axis of the bracket 10, is used to cut the occlusal edge of the occlusal tiewing 22 (including the rounded corners shown in FIGS. 2) as well as to cut along portions corresponding to the end surface 38 of the head 30, and mesial and distal sides of the shank 28 so that mesial and distal notches in the hook 26 are formed. Next, the brackets 10 are cut from the ring into individual parts, tumbled and polished, and then heat treated. The mesh base 12 is then brazed to the lingual side of the body 14.

We claim:

1. An orthodontic bracket comprising a base, a body extending from the base and a tiewing extending from the body, said bracket including a hook connected to said tiewing, said hook including an elongated shank and a head, said head having a mesiodistal width that is greater than the mesiodistal width of said shank and a labiolingual depth that is greater than the labiolingual depth of said shank, said hook and said tiewing being integrally formed during a machining operation, and wherein said shank includes fillets integrally connected to said tiewing and fillets integrally connected to said head.

2. The bracket of claim 1, wherein said head includes a generally cylindrical surface that extends about a reference axis generally perpendicular to an occlusal reference plane of the bracket when viewed toward its labial side.

3. The bracket of claim 1, wherein said shank has a rectangular cross-section in reference planes transverse to the longitudinal axis of said shank.

4. An orthodontic bracket comprising a base, a body extending from the base and a tiewing extending from the body, said bracket including a hook connected to said tiewing, said hook including an elongated shank and a head, said head having a mesiodistal width that is greater than the mesiodistal width of said shank and a labiolingual depth that is greater than the labiolingual depth of said shank, said hook and said tiewing being integrally formed during a machining operation, wherein said head includes an outermost gingival surface having a general shape of a partial cylinder.

5. A method for making an orthodontic bracket having a hook comprising the steps of:

shaping stock to form surfaces generally corresponding to labial sides of an occlusal and a gingival tiewing of the bracket, as well as to form surfaces generally corresponding to labial and lingual sides of a hook of the bracket;

cutting the stock along spaced apart reference lines to form surfaces generally corresponding to mesial and distal sides of occlusal and gingival tiewings of the bracket and also to remove portions of the stock located on mesial and distal sides of the hook;

moving a cutting tool along a path generally parallel to the labial surface of the bracket in order to form surfaces generally corresponding to an occlusal edge of the occlusal tiewing, a gingival edge of the hook, and a pair of notches of the hook; and moving a cutting tool along a path about an axis generally perpendicular to the occlusal plane of the bracket when viewed toward a labial side of the bracket to form surfaces generally corresponding to mesial, distal, labial and lingual surfaces of a head of the hook.

6. The method of claim 5, wherein said step of cutting the stock along spaced apart reference lines includes the step of rotating a rotary cutter.

7. The method of claim 5, wherein said step of moving a cutting tool along a path about an axis generally perpendicular to the occlusal plane includes the step of moving the cutting tool along a circular path.

8. The method of claim 5; including the step of changing the orientation of the stock after the step of moving a cutting tool along a path generally parallel to the labial surface of the bracket, and before the step of moving a cutting tool along a path about an axis generally perpendicular to the occlusal plane.

9. The method of claim 5, wherein said step of shaping stock includes the step of shaping round stock in a lathe.

* * * * *